(12) United States Patent
Dempster et al.

(10) Patent No.: US 6,910,373 B2
(45) Date of Patent: Jun. 28, 2005

(54) APPARATUS AND METHODS FOR REPEATABLE DOOR CLOSURE IN A PLETHYSMOGRAPHIC MEASUREMENT CHAMBER

(75) Inventors: Philip T. Dempster, Concord, CA (US); Mark Lowe, Danville, CA (US)

(73) Assignee: Life Measurement, Inc., Concord, CA (US)

(*) Notice: Subject to any disclaimer, the term of this patent is extended or adjusted under 35 U.S.C. 154(b) by 190 days.

(21) Appl. No.: 10/036,352

(22) Filed: Dec. 31, 2001

(65) Prior Publication Data

US 2003/0121321 A1 Jul. 3, 2003

(51) Int. Cl.[7] .......................... G01F 17/00; E05D 3/06; E05D 7/04; E05C 17/56
(52) U.S. Cl. ..................... 73/149; 16/235; 16/238; 16/240; 16/245; 16/246; 24/303; 292/251.5; 292/252
(58) Field of Search .......................... 73/149; 16/233, 16/235, 238, 240, 245, 246; 24/303; 292/251.5, 252

(56) References Cited

U.S. PATENT DOCUMENTS

| | | | | |
|---|---|---|---|---|
| 375,038 A | * | 12/1887 | Wright | 16/246 |
| 406,247 A | * | 7/1889 | Webb | 16/287 |
| 590,572 A | * | 9/1897 | Henry | 16/282 |
| 943,807 A | * | 12/1909 | Bommer | 16/282 |
| 1,155,161 A | * | 9/1915 | Ramsey | 49/246 |
| 1,249,815 A | * | 12/1917 | Otte | 16/282 |
| 2,164,047 A | * | 6/1939 | Baumann | 16/261 |
| 2,277,176 A | * | 3/1942 | Wagner | 16/366 |
| 2,372,431 A | * | 3/1945 | Kahle | 16/371 |
| 2,373,955 A | * | 4/1945 | Fuller | 16/238 |
| 2,930,074 A | * | 3/1960 | Marks | 16/263 |
| 3,511,237 A | * | 5/1970 | Jaeger | 600/533 |

(Continued)

FOREIGN PATENT DOCUMENTS

| | | | | |
|---|---|---|---|---|
| EP | 556679 A1 | * | 8/1993 | ............. E05D/3/06 |
| FR | 2571417 A1 | * | 4/1986 | ............. E05D/3/02 |
| JP | 03063370 A | * | 3/1991 | ........... E05C/19/16 |

OTHER PUBLICATIONS

Bailey et al., "Test–Retest Reliability of Body Fat Percentage Results Using Dual Energy X–Ray Absorptiometry and the BOD POD," *Presented at the American College of Sports Medicine, 48th Annual Meeting*, May 30–Jun. 2, 2001 in Baltimore, Maryland (abstract only).

Biaggi et al., "Comparison of Air–Displacement Plethysmography with Hydrostatic Weighing and Bioelectrical Impedance Analysis for the Assessment of Body Composition in Healthy Adults 1–3," *American Journal of Clinical Nutrition* vol. 69: pp. 898–903 (1999).

Dempster et al., "A New Air Displacement Method for the Determination of Human Body Composition," *Med Sci Sports Exerc*. Dec. 1995; 27(12): 1692–7.

(Continued)

*Primary Examiner*—Hezron Williams
*Assistant Examiner*—David A. Rogers
(74) *Attorney, Agent, or Firm*—Fish & Neave IP Group; Mark D. Rowland; Ropes & Crau LLP

(57) ABSTRACT

Apparatus and methods for generating repeatable closure of a volume measurement chamber are provided. More particularly, in one embodiment of the present invention, a dual articulating hinge is used to affix a chamber door to a volume measurement chamber, providing repeatable closure of a chamber door. In another embodiment of the invention, a laterally compliant magnetic latch is used to fasten a chamber door to a volume measurement chamber. In a third embodiment, a chamber door lid is mounted to a hinge bar via a ball joint, allowing the chamber door lid to self center about the chamber opening.

26 Claims, 8 Drawing Sheets

U.S. PATENT DOCUMENTS

| | | | | | |
|---|---|---|---|---|---|
| 3,577,840 | A | * | 5/1971 | Buberniak | 16/332 |
| 3,619,853 | A | * | 11/1971 | Merrill | 16/366 |
| 3,769,834 | A | * | 11/1973 | Fletcher et al. | 600/587 |
| 3,832,756 | A | * | 9/1974 | Lew | 16/297 |
| 4,144,749 | A | * | 3/1979 | Whitmore | 73/149 |
| 4,184,371 | A | | 1/1980 | Brachet | |
| 4,242,773 | A | * | 1/1981 | Beigh | 16/371 |
| 4,369,652 | A | | 1/1983 | Gundlach | |
| 4,406,289 | A | | 9/1983 | Wesseling et al. | |
| 4,458,396 | A | | 7/1984 | Aoki | |
| 4,506,408 | A | | 3/1985 | Brown | |
| 4,532,675 | A | * | 8/1985 | Salazar | 16/335 |
| 4,539,997 | A | | 9/1985 | Wesseling et al. | |
| 4,640,130 | A | | 2/1987 | Sheng et al. | |
| 4,676,253 | A | | 6/1987 | Newman et al. | |
| 4,700,436 | A | | 10/1987 | Morita | |
| 4,754,532 | A | | 7/1988 | Thomson et al. | |
| 4,794,669 | A | * | 1/1989 | Sanders | 16/341 |
| 4,800,624 | A | * | 1/1989 | Whitefoot et al. | 16/332 |
| 4,825,507 | A | * | 5/1989 | Killingstad | 16/241 |
| 4,825,526 | A | | 5/1989 | Shenier et al. | |
| 4,837,893 | A | * | 6/1989 | Wilson | 16/240 |
| 4,841,982 | A | | 6/1989 | Nikiforov et al. | |
| 4,888,718 | A | | 12/1989 | Furuse | |
| 4,915,431 | A | * | 4/1990 | Bailey | 292/251.5 |
| 4,972,842 | A | | 11/1990 | Korten et al. | |
| 5,018,243 | A | * | 5/1991 | Anspaugh et al. | 16/335 |
| 5,105,825 | A | | 4/1992 | Dempster | |
| 5,109,572 | A | | 5/1992 | Park | |
| 5,184,855 | A | * | 2/1993 | Waltz et al. | 292/251.5 |
| 5,379,777 | A | | 1/1995 | Lomask | |
| 5,450,750 | A | | 9/1995 | Abler | |
| 5,600,870 | A | | 2/1997 | Fields et al. | |
| 5,611,114 | A | * | 3/1997 | Wood et al. | 16/366 |
| 5,611,120 | A | | 3/1997 | Riceman et al. | |
| 5,611,582 | A | * | 3/1997 | Frolov et al. | 292/251.5 |
| 5,620,005 | A | | 4/1997 | Ganshorn | |
| 5,631,614 | A | | 5/1997 | Goodman et al. | |
| 5,703,735 | A | | 12/1997 | Bleeke | |
| 5,727,289 | A | * | 3/1998 | Reder | 16/375 |
| 6,013,905 | A | * | 1/2000 | Oster | 219/651 |
| 6,202,255 | B1 | * | 3/2001 | Sitter | 16/242 |
| 6,233,784 | B1 | | 5/2001 | Daoud | |
| 6,314,615 | B1 | | 11/2001 | Wolda | |
| 6,364,345 | B1 | * | 4/2002 | Lang | 280/728.3 |

OTHER PUBLICATIONS

Dewit et al., "Whole Body Air Displacement Plethysmography Compa5red with Hydrodensitometry for Body Composition Analysys," *Archives of Disease in Childhood* vol. 82 No. 2: pp. 159–164 (Feb. 2000).

Ellis et al., "Can Air–Displacement Plethysmography Replace Hydrodensitometry for Body Composition Analysis in Children and Adults," *Presented at Experimental Biology 2001 in Orlando, Florida* (abstract only).

Fields et al., "Body Composition Techniques and the Four–Compartment Model in Children," *Journal of Applied Physiology* vol. 89: pp. 613–620 (2000).

Gundlach, "The Plethysmometric Measurement of Total Body Volume," *Human Biology* 38(5): pp. 783–799.

Higgins et al., "Effect of Scalp and Facial Hair on Air Displacement Plethysmography Estimates of Percentage Body Fat," *Obes Res* May 2000; 9(5): 326–330.

http://academic.wsc.edu/hpls/glass_s/onlineped103/chapter4.htm, "What Fat is Linked to; Slides 4, 13–17, 20, 21, 23, 26, 28, 30" (Dec. 26, 2001).

http://www.geocities.com/HotSprings/5484/thesis/thesis2.htm, "Chapter II: Review of Literature on Body Composition" (Dec. 26, 2001).

http://hnrc.tufts.edu, "Laboratories and Programs: Body Composition Research Program" (Dec. 26, 2001).

http://www.nal.usda.gov/ttic/tektran/data/000009/27/0000092775.html, "Tektran Agriculture Research Service: Body Composition in Children and Adults by Air Displacement Plethysmography" (Dec. 26, 2001).

http://www.coe.uh.edu/~bsekula/pep6301/Ch.%2027%20Mkk.htm, "Body Composition Assessment" (Dec. 26, 2001).

http://odp.od.nih.gov/consensus/ta/015/015_intro.htm, "State of the Science Statements NIH Consensus Development Program: Bioelectrical Impedance Analysis in Body Composition Measurement—Dec. 12–14, 1994: 15. Bioelectrical Impedance Analysis in Body Composition Measurement" (Dec. 26, 2001).

http://brc.montana.edu/olympics/physiology/pb03.html, "Physiology & Psychology Performance Benchmarks: Body Composition and Body Mass" (Dec. 26, 2001).

LeCheminant et al., "Differences in Body Fat Percentage Measured Using Dual Energy X–Ray Absorptiometry and the BOD POD in 100 Women," *Presented at the American College of Sports Medicine 48th Annual Meeting*, May 30–Jun. 2, 2001 in Baltimore, Maryland (abstract only).

Lockner et al, "Comparison of Air–Displacement Plethysmography, Hydrodensitometry, and Dual X–ray Absorptiometry for Assessing Body Composition of Children 10 to 18 Years of Age," *Annals of the New York Academy of Sciences vol. 904—In Vivo Body Composition Studies*: pp. 72–78 (May 2000).

Maddalozzo et al., "Concurrent Validity of the BOD POD and Dual Energy X–Ray Absorptiometry Techniques for Assessing the Body Fat Percentage in Young Women," *Presented at the American College of Sports Medicine 48th Annual Meeting*, May 30–Jun. 2, 2001 in Baltimore, Maryland (abstract only).

McCrory et al., "Evaluation of a New Air Displacement Plethysmograph for Measuring Human Body Composition," *Med Sci Sports Exerc.* Dec. 1995; 27(12): 1686–91.

McCrory et al., "Comparison of Methods for Measuring Body Composition Responses to Progressive Resistance Training in Hispanic Elders with Type 2 Diabetes," *Presented at Experimental Biology 2001 in Orlando, Florida* (abstract only).

Miyatake et al., "A New Air Displacement Plethysmograph for the Determination of Japanese Body Composition," *Diabetes Obes Metab* Nov. 1999; 1(6): 347–51.

Nicholson et al., "Estimation of Body Fatness by Air Displacement Plethysmography in African American and White Children," *Pediatric Research* vol. 50 No. 4: pp. 467–473 (2001).

Nunez et al., "Body Composition in Children and Adults by Air Displacement Plethysmography," *Eur J Clin Nutr*. May 1999; 53(5): 382–7.

Wagner et al., "Techniques of Body Composition Assessment: A Review of Laboratory and Field Methods," *Research Quarterly for Exercise and Sport*: pp. 135–149 (Jun. 1999).

Yee et al., "Calibration and Validation of an Air-Displacement Plethysmography Method for Estimating Percentage Body Fat in an Elderly Population: A Comparison among Compartmental Models 1–3" *American Journal of Clinical Nutrition* vol. 74: pp. 637–642 (2001).

\* cited by examiner

APPARATUS AND METHODS FOR REPEATABLE DOOR CLOSURE IN A PLETHYSMOGRAPHIC MEASUREMENT CHAMBER

FIELD OF THE INVENTION

This invention relates generally to apparatus and methods for providing repeatable volume within an enclosed chamber. More specifically, the present invention provides apparatus and methods for providing repeatable door closure in a plethysmographic chamber to enhance the accuracy of body composition measurements.

BACKGROUND OF THE INVENTION

The assessment of body composition, including measurement of fat and fat-free mass, provides physicians with important information regarding physical status. Excess body fat has been associated with a variety of disease processes, such as cardiovascular disease, is diabetes, hypertension, hyperlipidemia, kidney disease, and musculoskeletal disorders. Low levels of fat free mass have been found to be critically adverse to the health of certain at-risk populations, such as the elderly, infants, and those suffering from muscle wasting diseases.

Assessment of body composition has also been found to be useful in the context of evaluating and improving athletic performance. Generally, athletes require a high strength to weight ratio to achieve optimal athletic performance. Because body fat adds weight without a commensurate increase in strength, low body fat percentages have been emphasized within many athletic fields. However, too little body fat can result in deterioration of both health and athletic performance. Thus, accurate measurement of body composition has been found extremely useful in analysis of athletic performance.

A variety of methods are currently used in the assessment of body composition. One common method is a skinfold measurement, typically performed using calipers that compress the skin at certain points on the body. While non-invasive, this method suffers from poor accuracy on account of variations in fat patterning, misapplication of population specific prediction equations, improper site identification for compressing the skin, poor fold grasping, and the necessity for significant technician training to administer the test properly.

Another method employed is bioelectric impedance analysis ("BIA"). Bioelectric impedance measurements rely on the fact that the body contains intracellular and extracellular fluids that are capable of conducting electricity. By passing a high frequency electric current through the body, BIA determines body composition based on the bodies, measured impedance in passing current, and the known impedance values for human tissue. However, the accuracy of this method is greatly affected by the state of hydration of the subject, and variations in temperature of both the subject and the surrounding environment.

The most common method currently used when precision body mass measurements are required is hydrostatic weighing. This method is based upon the application of Archimedes principle, and requires weighing of the subject on land, repeated weighing of the subject under water, and an estimation of air present in the lungs of the subject using gas dilution techniques. However, hydrodensitometry is time consuming, typically unpleasant for the subjects, requires significant subject participation such as repeated, complete exhalation of air from the subject's lungs, requires considerable technician training and, due to the necessary facilities for implementation, is unsuitable for clinical practice. Further, its application to populations who would particularly benefit from body-mass measurement, such as the obese, elderly, infants, or cardiac patents, is precluded by the above concerns.

One technique offering particular promise in performing body mass measurement is the use of plethysmography. Plethysmographic methods determine body composition through application of Boyle's law to the differentiation in volume between the volume of an empty measurement chamber, and the volume of the chamber with the subject to be measured inside. Examples of this technique are disclosed in U.S. Pat. No. 4,369,652 issued to Gundlach, U.S. Pat. No. 5,450,750 issued to Abler, U.S. Pat. No. 4,184,371 issued to Brachet, and U.S. Pat. No. 5,105,825 issued to Dempster. This procedure, in contrast to hydrodensitometry, generally does not cause anxiety or discomfort in the subject, and due to the ease and non-invasiveness of the technique, can readily be applied to populations for whom hydrodensitometry is impractical.

However, to the present, plethysmographic methods have demonstrated problems with accuracy. For example, failure to take into account differences in compressibility of air in the chamber as opposed to air in the lungs of the subject can result in significant variability in measurements. Although some effort has been made to address these considerations, as disclosed by Dempster, U.S. Pat. No. 5,105,825, the greatest practical impediment to widespread application of plethysmography is the necessity for repeatable, precise volume within the measurement chamber.

As noted by Gundlach, et al., "The Plethysmometric Measurement of Total Body Volume," Human Biology, Vol. 38, No. 5, p.783–99, large variations in measured body composition occur based on small changes of volume in the measurement chamber, due to nonrepeatability in the closing action employed for measurement chambers. Variability in closure pressure, and various stresses and strains in both the chamber door and chamber wall for plethysmographic chambers likewise contribute to the inaccuracy of body composition measurements. While current plethysmographic systems have to a certain degree been able to provide mechanical stability with respect to the method of ingress and egress necessary to generate accurate measurements, such systems are typically very complex, expensive, and labor-intensive to manufacture.

In view of the foregoing drawbacks, it would be desirable to provide apparatus and methods for accurate, non-invasive determination of body mass.

It would further be desirable to provide apparatus and methods for providing repeatable door closure in a plethysmographic chamber to ensure accurate, precise volume measurements.

It would further be desirable to provide robust, inexpensive, and easy to manufacture systems for providing repeatable door closure in a plethysmographic chamber.

SUMMARY OF THE INVENTION

It is an object of the present invention to provide apparatus and methods for accurate, non-invasive determination of body mass.

It is another object of the present invention to provide apparatus and methods for providing repeatable door closure in a plethysmographic chamber to ensure accurate, precise volume measurements.

It is still another object of the present invention to provide robust, inexpensive, and easy to manufacture systems for providing repeatable door closure in a plethysmographic chamber.

These and other objects of the present invention are accomplished by providing systems and methods for generating repeatable, accurate door closure in a plethysmographic chamber.

One embodiment of the apparatus and methods of the present invention comprises one or more dual-articulating hinges mounted to closable means of entry for a plethysmographic chamber, said hinges providing repeatable, solid location of the means of entry upon closure.

A second embodiment of the present invention involves the use of one or more laterally compliant magnetic latches for fastening the means of chamber entry to the chamber wall.

A third embodiment of the apparatus and methods of the present invention comprises a spring loaded, self-aligning door that likewise generates repeatable door closure.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1A:
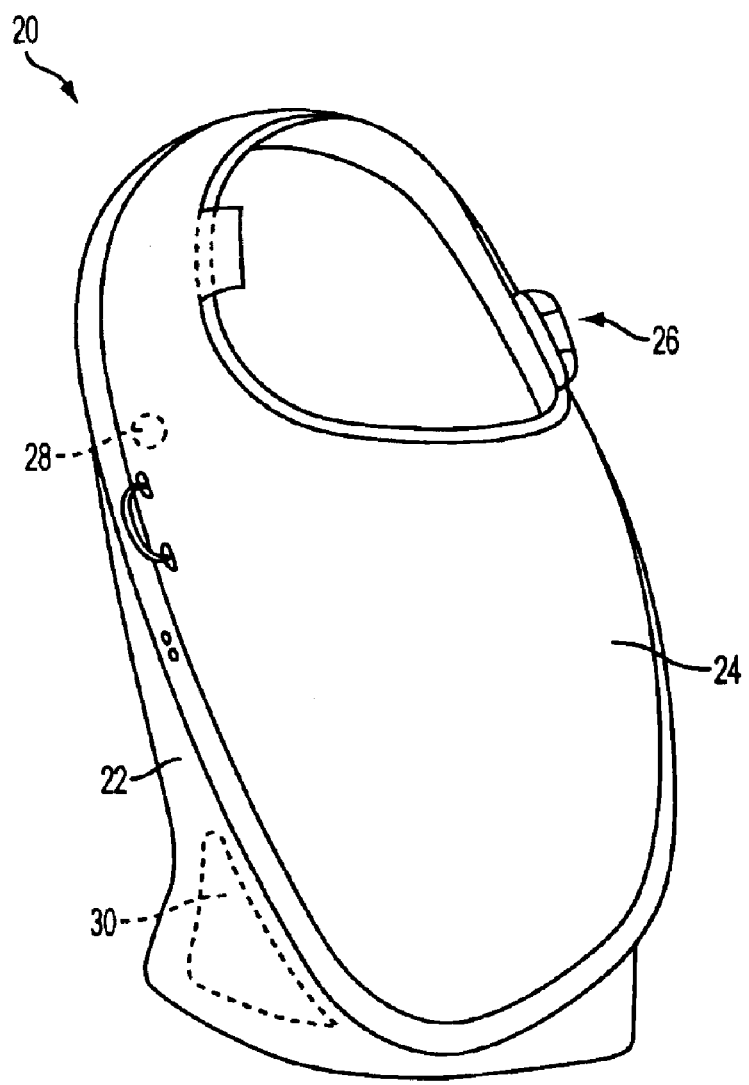
FIG. 1A is a representation of a plethysmographic chamber in which embodiments of the present invention operate.

Referring to FIG. 1A, a representational view of the plethysmographic chamber in which embodiments of the present invention operate is described.

Plethysmographic chamber 20 is composed of chamber wall 22, chamber door 24, hinge 26, latch 28, and plethysmographic measurement components 30. Chamber wall 22 and chamber door 24 may be constructed of any suitably rigid material, such as plywood, molded fiberglass, aluminum, etc. Further, chamber door 24 may contain transparent panels constructed of a translucent material such as glass, plexiglass, or polycarbonate.

Figure 1B:
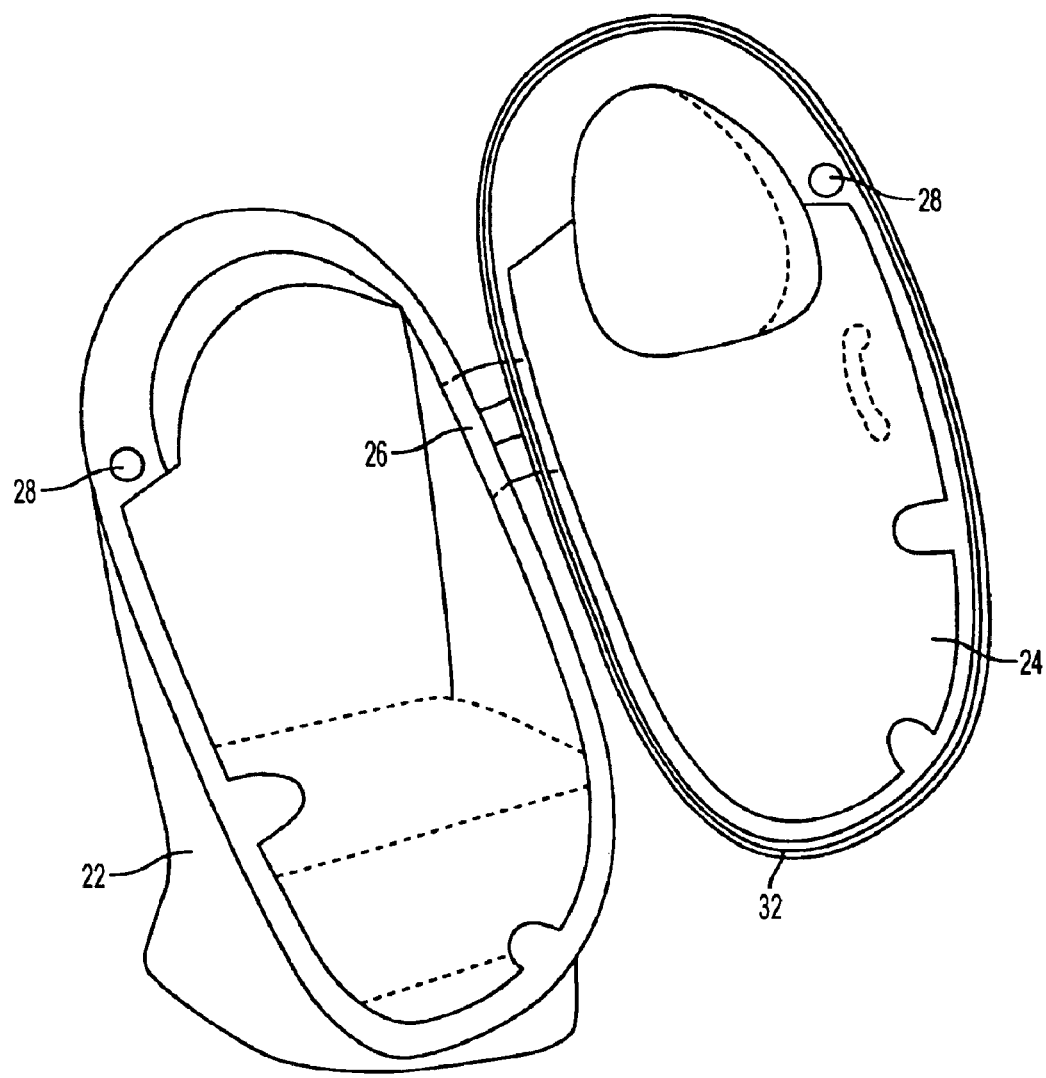
FIG. 1B is a representational view of the plethysmographic chamber of the present invention with the chamber door in the open position.

As can be seen more clearly in FIG. 1B, a representation of the chamber of the present invention with the chamber door in the open position, dual-articulating hinge 26 permanently affixes chamber door 24 to chamber wall 22, and allows chamber door 24 to open and close, providing for entry of the subject to be measured into chamber 20.

Laterally compliant magnetic latch 28, located on the opposite side of chamber 22 from hinge 26, fastens chamber door 24 to chamber wall 22 when chamber door 24 is in the closed position.

Further, upon closure of chamber door 24, gasket 32, affixed about the circumference of chamber door 24, is inflated to a fixed pressure, creating a seal between chamber door 24 and chamber wall 22.

Although one hinge and one latch are shown in the illustrations of FIGS. 1A and 1B, one of ordinary skill in the art would recognize that multiple hinges and/or multiple latches could be used in accord with the present inventions.

Further, one of skill in the art would recognize that the dual articulating hinge and magnetic latch of the present invention could be used either in combination with or separately from each other in accord with the present inventions. In the preferred embodiment, two hinges are used to create stability across the plane of closure between door 24 and wall 22, in conjunction with two laterally compliant latches.

Figure 2A:
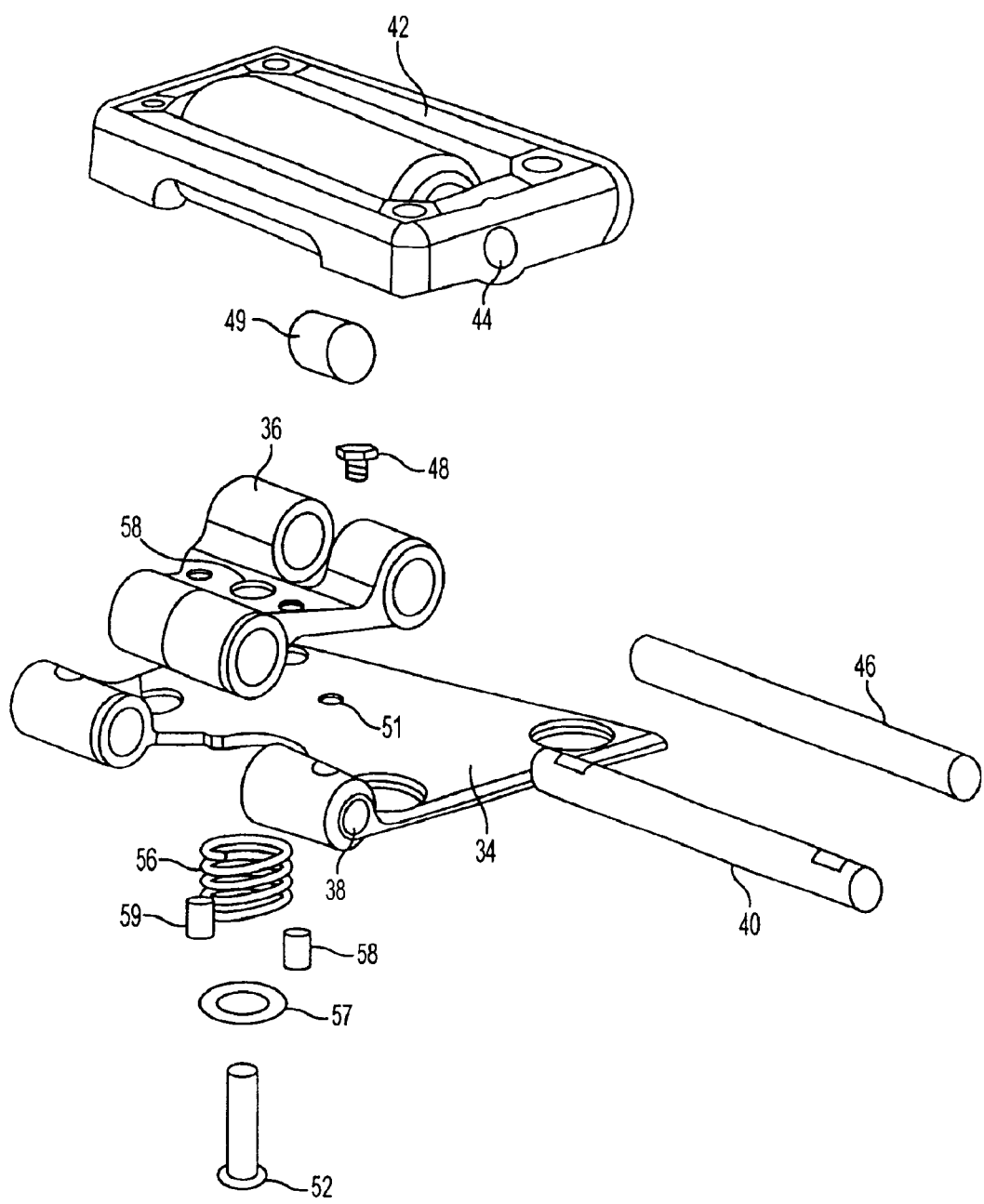
FIG. 2A is an exploded view of the dual-articulating hinge of the present invention.

Referring now to FIG. 2A, an exploded view of the dual articulating hinge of the present invention is described. Inner hinge leaf 34 is connected to hinge coupling strut 36 at hinge 38 by means of hinge pin 40. Rotational movement about hinge 38, therefore, provides a first degree of articulation. Hinge coupling strut 36 is connected to outer hinge leaf 42 at hinge 44 by means of hinge pin 46. Rotational movement about hinge 44 defines a second degree of articulation.

In order to accurately and repeatedly define the clearance between chamber door 24 and chamber wall 22, a spacer 48 is coupled to inner hinge leaf 34. When chamber door 24 is closed, spacer 48 makes contact with contact member 49 on outer hinge leaf 42, thereby defining the distance between chamber door 24 and chamber wall 22. Preferably spacer 48 is adjustable, to allow for user selectable setting of the clearance between chamber door 24 and chamber wall 22. For example, spacer 48 could be a bolt whose height can be adjusted by tightening or loosening the bolt into a threaded insert 51 in the inner hinge leaf 34.

Figure 2B:
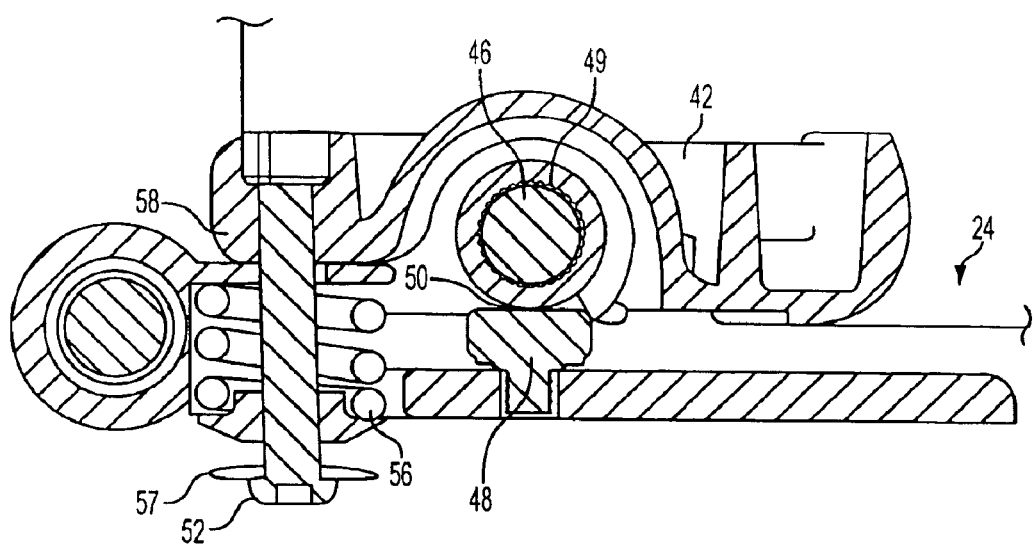
FIG. 2B is a cross-sectional view of the dual-articulating hinge of the present invention.

Referring now to FIG. 2B, a cross-sectional view of the dual-articulating hinge of the present invention is described. As set forth above, when chamber door 24 is in the process of being closed, spacer 48 makes contact at a contact point 50 on outer hinge leaf 44.

In the preferred embodiment, contact member 49 comprises a load bearing member, such as a roller bearing, mounted on hinge pin 46. As door 24 is closed, and spacer 48 makes contact with the load bearing member, the load bearing member can rotationally pivot about hinge pin 46, and therefore is able to lessen stress in the plane of closure while bearing the load presented at spacer 48.

Further, it is preferred that some tension be applied in the degree of articulation defined by hinge 46 to provide more repeatable door closure position, and to minimize scrubbing of gasket 32. In the preferred embodiment, hinge spring 56 is mechanically coupled to hinge coupling strut 36 by means of retaining screw 52, which passes through both the bore of hinge spring 56 and through gap 58 in hinge coupling strut 36, and is coupled directly to upper hinge leaf 42. As door 24 is being closed, upper hinge leaf 42 rotates in the degree of articulation defined by hinge 44. Spring 56 is, therefore, compressed by the head of retaining screw 52 on account of the rotation about hinge 44, providing for greater repeatability of door closure. Alternatively, a washer 57 can be used in conjunction with retaining screw 52 to compress spring 56.

Further, as one of ordinary skill in the art would recognize, other methods of providing tension in the degree of the articulation in order to facilitate repeatable door closure can be used in accordance with the present invention. For example, a torsion spring can be used in conjunction with hinge 44 to provide the desired tension in the second degree of articulation. Alternatively, a leaf spring could be used in conjunction with upper hinge leaf 42 to generate the required tension.

Referring back to FIG. 2A, it is preferable that hinge spring 56 be precompressed to minimize the effort necessary to close door 24. Thus, in a preferred embodiment, a pair of adjustable set screws, 58 and 59, are mounted through hinge coupling strut 36, such that set screws 58 and 59 make contact with upper hinge leaf 42, thereby setting a minimum gap between coupling strut 38 and upper hinge leaf 42, and precompressing hinge spring 56. This precompression of hinge spring 56 makes door closure easier, and also assists in minimizing scrubbing of the gasket 32.

Alternatively, one of ordinary skill in the art would recognize that the structure and function of hinge 42 and hinge coupling strut 36, defining the second degree of articulation, could be performed by a leaf spring solidly affixed to upper hinge leaf 42 at one end, and terminating at hinge 38 (which defines the first degree of articulation) at the other end, and still remain within the scope of the invention.

Figure 3A:
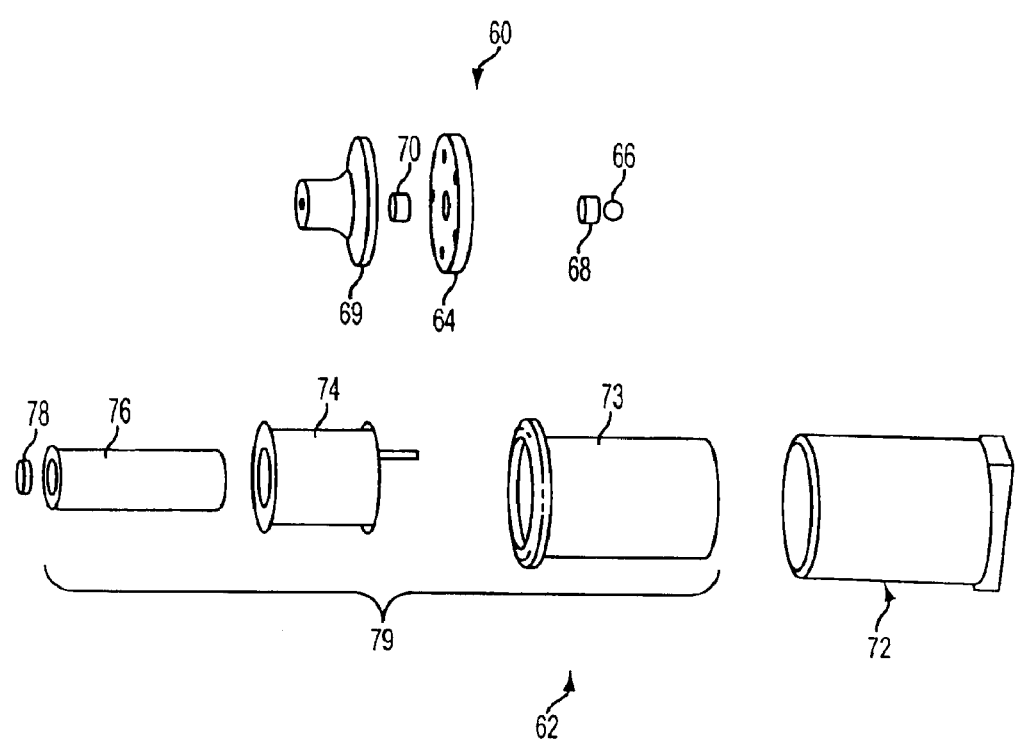
FIG. 3A is an exploded view of the laterally compliant magnetic latch of the present invention.

Referring now to FIG. 3A, a detailed view of the magnetic latch of the present invention is described. Magnetic latch 28 is comprised of a first latch member 60 and a second latch member 62.

In a preferred embodiment, first latch member 60 is affixed to chamber door 24, and second latch member 62 is affixed to chamber wall 22, such that when door 24 is in the closed position, latch 28 fastens chamber door 24 to chamber wall 22. Alternatively, first latch member 60 can be located on chamber wall 22 and second latch member 62 can be located on chamber door 24.

First latch member 60 consists of latch face plate 64, roller ball 66, sleeve 68, and latch mount 69. Roller ball 66 is housed in sleeve 68, which in turn is housed within the surface of latch face plate 64. Latch face plate 64 is coupled to latch mount 69, which is used to mount first latch member 60 to the plethysmographic chamber. In a preferred embodiment, first latch member 60 further comprises a plate 70, which is coupled between roller ball 66 and latch mount 69. Plate 70 is preferably made of the same hardened material as roller ball 66.

Sleeve 68 is made of rubber or other similarly pliant compound that allows for rotational movement of roller ball 66. Roller ball 66 is made of any suitably hard metal which will not deform under the stresses imparted by contact between first latch member 60 and second latch member 62, such as carbide or hardened steel. Any such deformation in roller ball 66 would hinder the ability of magnetic latch 28 to maintain lateral compliance.

Second latch member 62 is comprised of magnet housing 72, magnet outer pole piece 73, magnet coil 74, magnet inner pole piece 76, and insert plate 78. Insert plate 78 is made of similarly hard material as roller ball 66. Alternatively, the insert plate could be comprised of a hardened case surrounding the end of magnet inner pole piece 76 proximal to latch member 60 when latch 28 is in the closed position. The combination of magnet outer pole piece 73, magnet coil 74, magnet inner pole piece 76 form an electromagnet 79, the magnetic force of which serves to couple second latch member 62 and first latch member 60.

Figure 3B:
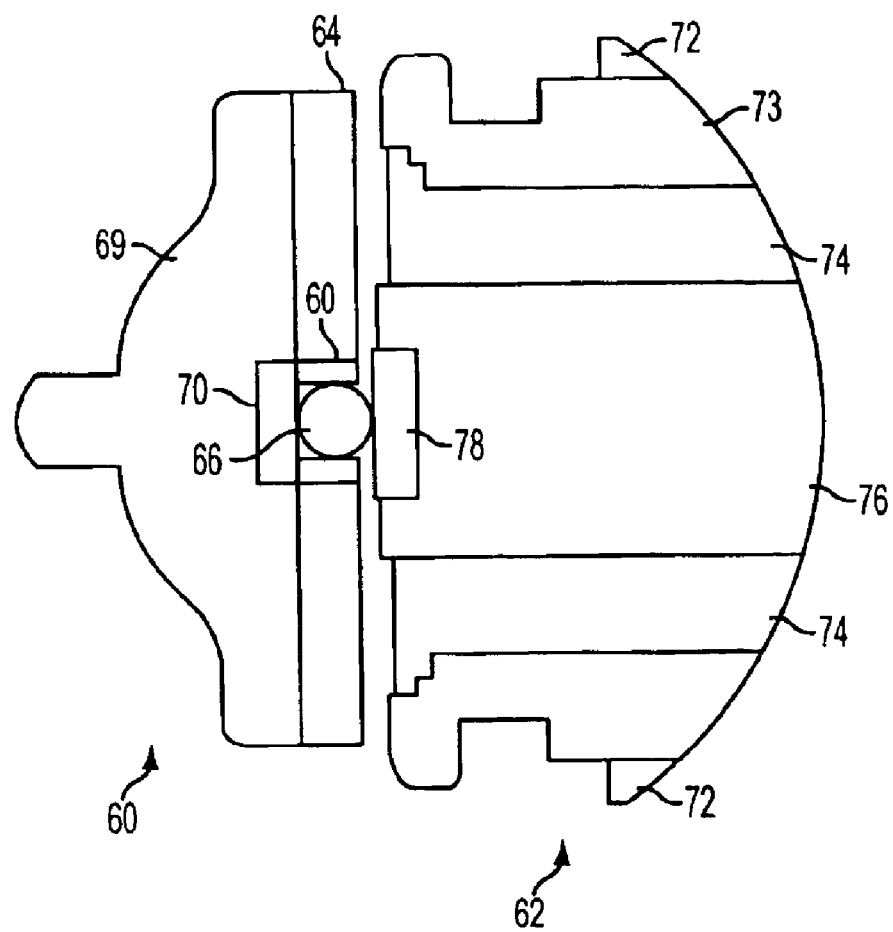
FIG. 3B is a cross-sectional view of the laterally compliant magnetic latch of the present invention in the closed position.

Referring now to FIG. 3B, a cross sectional view of the laterally compliant magnetic latch in the closed position is described. At the proximal end of second latch member 62 is an approximately planar surface comprised of insert plate 78, and proximal ends of magnet outer pole piece 73, magnet coil 74, and magnet inner pole piece 76. The term approximately planar in this instance means that all of the proximal end surfaces of magnet outer pole piece 73, magnet coil 74, magnet inner pole piece 76, and insert plate 78 are parallel with respect to each other and to the plane of closure (defined below), but that one or more of these surfaces may be offset such that the planar end of second latch member 62 is not a perfectly flat surface.

When latch 28 is in the closed position, the junction formed between latch face plate 64 of first latch member 60, and the approximately planar surface at the proximal end of second latch member 62 defines the plane of closure for magnetic latch 28. Although first latch member 60 and second latch member 62 are held together by the magnetic force of electromagnet 79, the surfaces of first latch member 60 and second latch member 62 only make contact with each other where roller ball 66 makes contact with insert plate 78, to allow for rotational movement by roller ball 66. This capability of roller ball 66 to rotate with respect to insert plate 78 relieves stress in the plane of closure caused by shifting, various stresses and strains on the chamber, deviations in chamber door shape, and differing application of pressure in a closing of the chamber door 24, while still maintaining compliance with respect to chamber closure volume.

In an alternative embodiment of the magnetic latch of the present invention, multiple roller balls are mounted in said latch face 68 to ensure lateral compliance.

Figure 4:
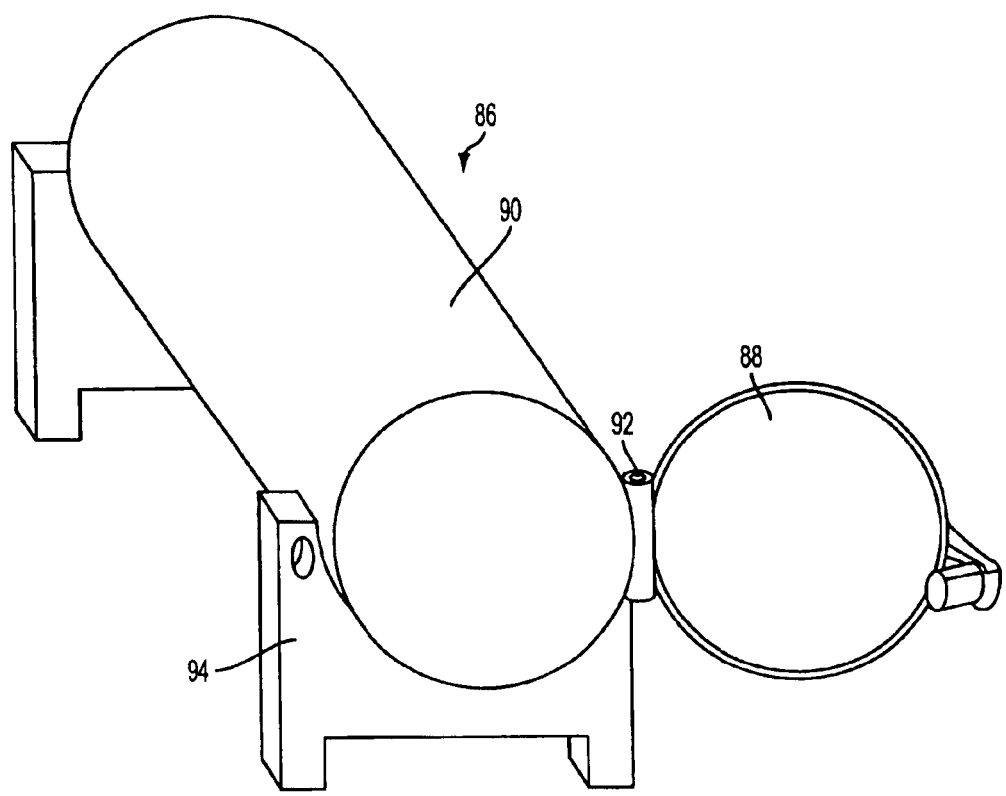
FIG. 4 is a representation of the infant sized plethysmographic chamber of the present invention.

Referring to FIG. 4, a representational view of the infant sized plethysmographic chamber is described. Plethysmographic chamber 86 is comprised of chamber door assembly 88, chamber 90, hinge 92, and door frame 94.

Figure 5A:
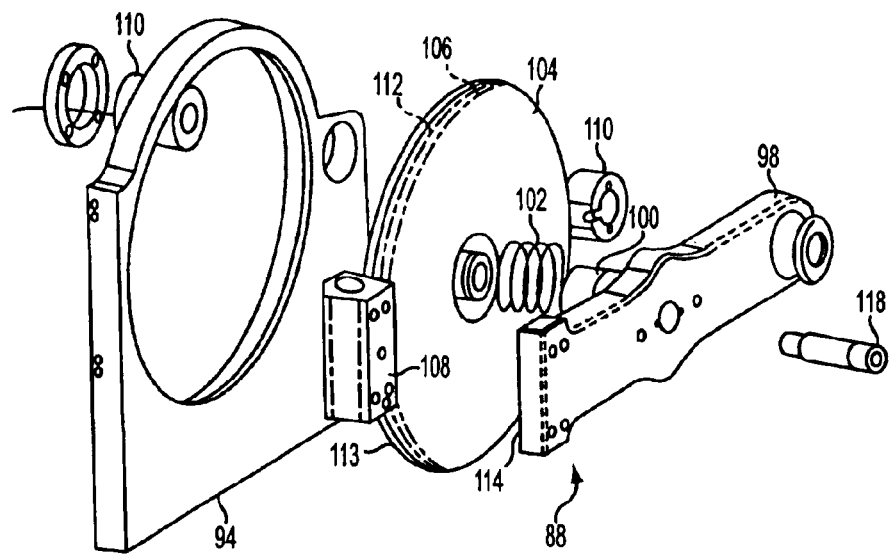
FIG. 5A is an exploded view of the spring-loaded, self-aligning door of the present invention.

In FIG. 5A, an exploded view of the self aligning chamber door of the present invention is presented. Door assembly 88 is comprised of hinge bar 98, ball joint 100, spring 102, door lid 104, seal 106 and door frame 94. Hinge bar 98 is mounted at one end of the chamber door frame 94 by means of hinge 108. When door assembly 88 is in the closed position, it is fastened to door frame 94 by means of magnetic latch 110.

In a preferred embodiment, door lid 104 is mounted pivotally to hinge bar 98 by means of ball joint 100. Further, door lid 104 is spring loaded about ball joint 100. Alternatively, door lid 104 could be mounted using any type of pivotal joint, such as a universal joint, a pointed pin in a drilled point, or a short spring, so long as the door lid can move pivotally with respect to the hinge bar.

Figure 5B:
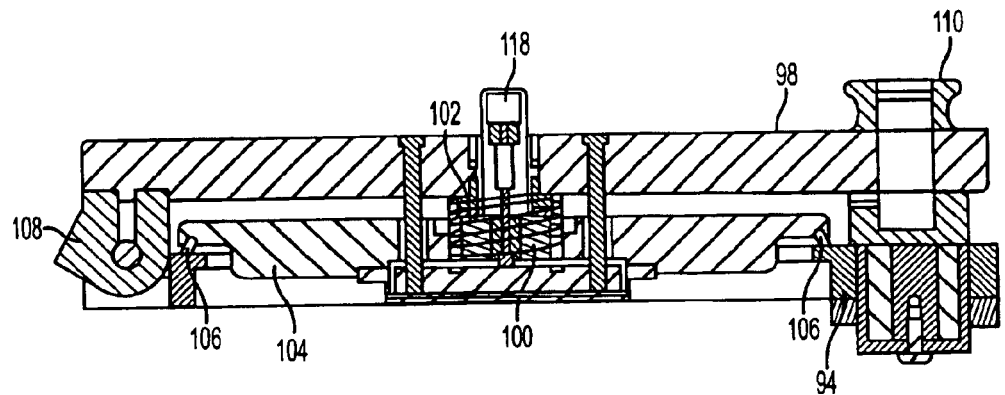
FIG. 5B is a cross-sectional view of the door assembly of the present invention.

Referring now to FIG. 5B, a cross sectional view of door frame 94 and door assembly 88 is described. Seal 106 is mounted about the inner circumference of door lid 104. When door assembly 88 is in the closed position, door lid 104, which is symmetrical with respect to ball joint 100, automatically self centers on standoffs 112–114 located about the rim of door lid 104, on account of door lid 104 being able to move pivotally with respect to hinge bar 98. In the preferred embodiment, three standoffs are used to provide for the greatest stability and repeatability of closure.

Seal 106 makes contact with door frame 94 about the circumference of door frame 94. As shown in FIG. 5B, the shape of the inner surface of door lid 104 can also be tapered to form a better seal with door frame 94. Further, spring 102, mounted about ball joint 100, applies a known force to compress seal 106 against door frame 94. On account of the self centering of door lid 104, and the known force applied to door lid 104 by spring 102, repeatable closure of door assembly 88 is obtained, providing repeatable volume measurements for chamber 86.

In a preferred embodiment of the present invention, a shock absorber 118 can be used to mount ball joint 100 to hinge bar 98. This shock absorption minimizes startling motions of door lid 104 when opening or closing door assembly 88.

Although the foregoing embodiments are discussed in the context of plethysmographic systems, one of ordinary skill in the art would recognize that these closure methods and apparatus would be equally useful in any chamber for which repeatable door closure is required.

Further, while preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A chamber for conducting repeatable volume measurements, the chamber comprising:
    a chamber wall;
    a chamber door; and
    a dual articulating hinge affixing said chamber door to said chamber wall, wherein said dual articulating hinge comprises a first hinge leaf, a second hinge leaf, and at least one spacer, and
    wherein said spacer defines a set distance between said first hinge leaf and said second hinge leaf, to repeatedly define a predetermined clearance between said chamber door and said chamber wall in a closed position.

2. The chamber of claim 1, further comprising:
    a gasket affixed about the circumference of said chamber door, said gasket providing a seal between said chamber door and said chamber wall.

3. The chamber of claim 1, wherein the dual articulating hinge further comprises:
    a hinge coupling strut;
    a first hinge pin for joining said first hinge leaf to said hinge coupling strut at a first hinge; and
    a second hinge pin for joining said hinge coupling strut to said second hinge leaf at a second hinge.

4. The chamber of claim 3, wherein said hinge further comprises:
    a load bearing surface on said second hinge leaf for bearing the load presented at said spacer.

5. The chamber of claim 4, wherein said load bearing surface is a roller bearing mounted about said second hinge pin.

6. The chamber of claim 4, wherein said hinge further comprises:
    a hinge spring; and
    a retaining screw passing through the bore of said spring, and mounted to said second hinge leaf.

7. The chamber of claim 6, wherein the retaining screw compresses said spring in a degree of articulation defined by motion about said second hinge pin.

8. The chamber of claim 1, further comprising: a latch for fastening said chamber door to said chamber wall when said door is in a closed position.

9. The chamber of claim 8, wherein said latch is a laterally compliant magnetic latch, comprising:
    a magnetic latch face, said latch face including:
        a sleeve; and
        a roller ball mounted in said sleeve, and capable of rotation within said sleeve;
    a magnet housing, said housing including:
        an electromagnet;
        a planar surface; and
    an insert in said planar surface, wherein said insert makes contact with said roller ball when said latch is closed, and wherein the planar surface of said magnet housing and the magnetic latch face form a plane of closure.

10. The chamber of claim 9, wherein said latch face makes contact with said magnet housing at a point defined by said roller ball and said insert.

11. The chamber of claim 1, wherein the predetermined clearance between said chamber door and said chamber wall is adjustable.

12. The chamber of claim 11 wherein said spacer comprises a bolt having a height that can be adjusted.

13. The chamber of claim 12 further comprising a threaded insert formed in said first hinge leaf, wherein said threaded insert is configured to receive said bolt.

14. A chamber for conducting repeatable volume measurements, the chamber comprising:
    a chamber wall;
    a chamber door; and
    a magnetic latch for fastening said chamber door to said chamber wall when said door is in a closed position,
    wherein said magnetic latch comprises at least one roller ball coupled to said chamber wall, and at least one substantially flat magnetic member coupled to said chamber door, and
    wherein said roller ball contacts said substantially flat magnetic member in the closed position.

15. The chamber of claim 14, wherein said latch further comprises:
    a magnetic latch face, said latch face including:
        a sleeve, wherein said roller ball is mounted in said sleeve, and capable of rotation within said sleeve;
    a magnet housing, said housing including:
        an electromagnet;
        a planar surface; and
    wherein said substantially flat magnetic member comprises an insert in said planar surface.

16. The chamber of claim 15, wherein said latch face makes contact with said magnet housing at a point defined by said roller ball and said insert.

17. The chamber of claim 14, further comprising:
    a gasket affixed about the circumference of said chamber door, said gasket providing a seal between said chamber door and said chamber wall.

18. The chamber of claim 14, further comprising a hinge affixing said chamber door to said chamber wall, wherein said door can rotate about said hinge.

19. The chamber of claim 18, wherein said hinge is a dual articulating hinge, comprising:
    a first hinge leaf;
    a second hinge leaf;
    a hinge coupling strut;
    a first hinge pin for joining said first hinge leaf to said hinge coupling strut at a first hinge;
    a second hinge pin for joining said hinge coupling strut to said second hinge leaf at a second hinge; and, a spacer for defining a set distance between said first hinge leaf and said second hinge leaf.

20. The chamber of claim 19, wherein said hinge further comprises:

a load bearing surface on said second hinge leaf for bearing the load presented at said spacer.

21. The chamber of claim 20, wherein said load bearing surface is a roller bearing mounted about said second hinge pin.

22. The chamber of claim 20, wherein said hinge further comprises:

a hinge spring; and a retaining screw passing through the bore of said spring, and mounted to said second hinge leaf.

23. The chamber of claim 22, wherein the retaining screw compresses said spring in a degree of articulation defined by motion about said second hinge pin.

24. The chamber of claim 14 wherein said roller ball rotates to allow movement of said substantially flat magnetic member when said chamber door is in the closed position.

25. The chamber of claim 24 wherein the movement of said substantially flat magnetic member coupled to said chamber door is permitted in any lateral direction, excluding a dimension in which said chamber door would move away from said chamber wall to cause said roller ball to no longer contact said substantially flat magnetic member.

26. A chamber for conducting repeatable volume measurements, the chamber comprising:

a chamber wall;

a chamber door; and a magnetic latch for fastening said chamber door to said chamber wall when said door is in a closed position, wherein said magnetic latch comprises at least one roller ball coupled to said chamber door, and at least one substantially flat magnetic member coupled to said chamber wall, and wherein said roller ball contacts said substantially flat magnetic member in the closed position.

* * * * *